United States Patent [19]

Underhill et al.

[11] Patent Number: 4,610,876

[45] Date of Patent: Sep. 9, 1986

[54] ATTRACTANTS FOR FALL CANKERWORM MOTHS

[75] Inventors: Edward W. Underhill; John W. Wong; Pachagounder Palaniswamy; Warren F. Steck; Melvin D. Chisholm, all of Saskatoon, Canada

[73] Assignee: Canadian Patents & Development Limited, Ottawa, Canada

[21] Appl. No.: 805,411

[22] Filed: Dec. 5, 1985

Related U.S. Application Data

[63] Continuation of Ser. No. 650,191, Sep. 13, 1984, abandoned.

[51] Int. Cl.$^4$ .................. A01N 27/00; C07C 11/21
[52] U.S. Cl. ............................ 424/84; 585/16; 585/508; 514/762
[58] Field of Search ............... 424/84; 585/16, 508; 514/762

[56] References Cited

U.S. PATENT DOCUMENTS

| | | | |
|---|---|---|---|
| 3,932,616 | 1/1976 | Meresz et al. | 424/355 |
| 3,996,270 | 12/1976 | Friedman et al. | 585/16 |
| 4,018,844 | 4/1977 | Meresz et al. | 585/16 |

OTHER PUBLICATIONS

Wong et al. Journal of Chemical Ecology, vol. 10, No. 3, pp. 463–473, 1984.

*Primary Examiner*—Howard T. Mars
*Attorney, Agent, or Firm*—Alan A. Thomson

[57] ABSTRACT

Two new compounds which are attractive to male fall cankerworm moths, *Alsophila pometaria*, in the field, are described. They are (Z,Z,Z,E)-3,6,9,11-nonadecatetraene and (Z,Z,Z,Z)-3,6,9,11-nonadecatetraene. These compounds, separately and together, and these two compounds together with a third, [(Z,Z,Z)3,6,9-nonadecatriene], act as attractants to male fall cankerworm moths and can be used to monitor, confuse or attempt to control, populations of the moths.

12 Claims, No Drawings

ATTRACTANTS FOR FALL CANKERWORM MOTHS

This application is a continuation of application Ser. No. 650,191 filed Sept. 13, 1984, now abandoned.

FIELD OF THE INVENTION

This invention is directed to artificial attractants for male fall cankerworm moths, Alsophila pometaria. These attractants can be used to monitor, control or confuse populations of male moths. Three novel compounds have been isolated and synthesized.

BACKGROUND AND PRIOR ART

In contrast to other major families of Lepidoptera where sex pheromones and sex attractants are known for several species, the pheromone of only one geometrid species, the winter moth, Operophtera brumata (L.) has been identified. This winter moth pheromone, (Z,Z,Z)-1,3,6,9-nonadecatetraene, constitutes another example of a new group of pheromone components, unsaturated hydrocarbons, which have been reported in the last few years from species of Arctiidae (Conner et al, Behav. Ecol. Sociobiol. 7, 55-63, 1980; A. S. Hill and W. L. Roelofs, J. Chem. Ecol. 7, 655-668, 1981; A. S. Hill et al, J. Chem. Ecol. 8, 383-396, 1982) and Noctuidae (R. R. Heath et al, J. Chem. Ecol. 9, 645-656, 1983; E. W. Underhill et al, J. Chem. Ecol. 9, 1413-1423, 1983). E. W. Underhill et al, at the National Meeting of the Entomological Society of America, in Toronto, November 1982, reported that males of 15 geometrid species gave strong electroantennograph (EAG) responses to one or more unsaturated $C_{18-22}$ hydrocarbons and monoepoxides substituted at positions 3, 6 and 9. Included in the group of responding geometrids was the fall cankerworm, Alsophila pometaria (Harris).

This unsaturated hydrocarbon group of pheromone components is quite distinct from the unsaturated alcohols and unsaturated alcoholic esters found to be active components of pheromone mixtures for such species as the sunflower moth (see: E. W. Underhill et al, Canadian Patent No. 1,139,659) and the darksided cutworm moth (see: G. E. Swailes and D. L. Struble, Canadian Patent No. 1,085,722).

Larvae of the fall cankerworm are major defoliators of ornamental trees in N. America, including elm, oak, apple, beech and linden. In late fall, when the temperature nears freezing, adult moths emerge and the vestigial-winged females climb trees or buildings where mating occurs and eggs are deposited. Methods of controlling populations of fall cankerworm have included use of Bacillus thuringiensis, insecticides and banding tree trunks to trap adult females. Population control by mating disruption using the insect's sex pheromone is another alternative. This may be particularly useful for fall cankerworm control since females cannot fly from non-treated areas into pheromone disrupted areas, a common drawback to this method.

SUMMARY OF THE INVENTION

This invention concerns polyunsaturated straight chain hydrocarbons of nineteen carbon atoms having double bonds in the 3, 6 and 9 positions in the Z-configuration, and the bond in the 11-position being selected from a double bond in the Z-configuration and a double bond in the E-configuration. Such a compound may be (Z,Z,Z,E)-3,6,9,11-nonadecatetraene (A) or (Z,Z,Z,Z)-3,6,9,11-nonadecatetraene (B), and an insect attractant may be formulated consisting of each compound separately or compound A in admixture with compound B. Other insect attractants may comprise a synergistically active proportion, preferably less than about 90% w/w based on the weight of synergistically interactive components (ideally about 33% w/w), of (Z,Z,Z)-3,6,9-nonadecatriene, in addition to at least one of compound A and compound B. The above insect attractants may be employed with a solid or liquid carrier. We have found a rubber carrier to be useful in conjunction with such insect attractants.

The above insect attractants may be employed in insect traps and, preferably, at least 30 μg of the attractant composition is employed in each trap.

The above insect attractants may be employed in a method of attracting fall cankerworm moths, during the flight season and in the expected locale of such moths, to at least one specific locus, which comprises baiting an insect trap with one of such insect attractants. The above insect attractants may also be employed in a method of confusing fall cankerworm moths, during the flight season and in the expected locale of such moths, comprising at least one of disseminating and baiting specific loci with at least one of such insect attractants.

DESCRIPTION OF THE INVENTION

Analysis of the sex pheromone of A. Pometaria has led to the isolation and identification of (Z,Z,Z,E)-3,6,9,11-nonadecatetraene (A), (Z,Z,Z,Z)-3,6,9,11-nonadecatetraene (B), and (Z,Z,Z)-3,6,9-nonadecatriene (C), as components of the natural pheromone (J. W. Wong et al, J. Chem. Ecol. 10, 463-474, 1984). The two tetraenic hydrocarbons (A and B) have not been previously described. The triene (C) has recently been identified as a component of the sex pheromone of the giant looper Boarmia (Ascotis) selenaria (Schiffermuller) by D. Becker et al, Tetrahedron Lett. 24, 5505-5508, 1983. Both D. Becker et al (op.cit.) and E. W. Underhill et al (op.cit.) discuss the preparation of the triene.

EXAMPLE 1

Preparation of (Z,Z,Z,E)-3,6,9,11-nonadecatetraene (A)

To an anhydrous solution of (Z,Z)-3,6-nonadienyltriphenylphosphonium bromide (2.69 g, 5.79 mmol), in a mixture of HMPA (15 ml) and THF (25 ml) at −45° C., was added 1.06 g (5.79 mmol) of sodium bis(trimethylsilyl)amide. The reaction mixture, which turned to a red-brown colour upon addition of the base, was stirred for 30 min at −45° C. and then treated with 0.89 g (5.79 mmol) of (E)-2-decenal. After 3 h, the reaction mixture, which had slowly warmed to 0° C., was diluted with water (30 ml) and extracted with hexane (3×20 ml). The hexane extract was washed with water (3×30 ml), dried over magnesium sulfate and concentrated to give crude A. Elution of the crude product through silica gel (15 cm×2.5 cm I.D. column) with hexane afforded 1.0 g (66.4%) of the tetraene A; PMR (360 MHz, $C_6D_6$) δ 6.47 (1H, dddd J = 15.0, 11.0, 2.6 and 1.4 Hz),

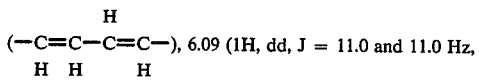
, 6.09 (1H, dd, J = 11.0 and 11.0 Hz,

-continued

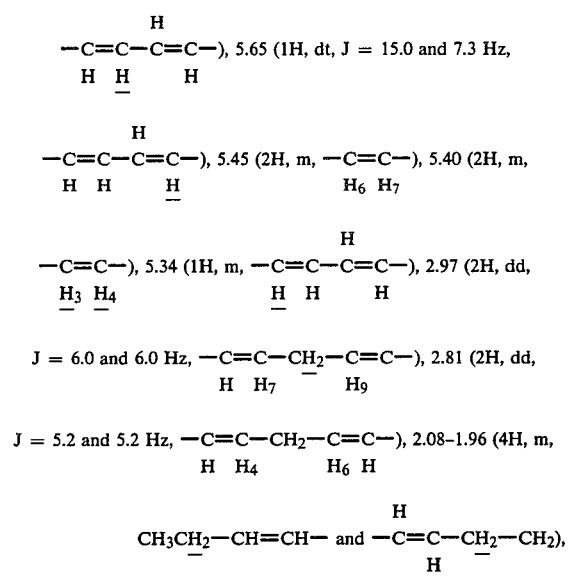

1.23 (10H), bs, $CH_3(CH_2)_5-$), 0.91 (3H, t, J=7.6 Hz, $CH_3CH_2-CH=CH$), 0.89 (3H, t, J=7.0 Hz, $-(CH_2)_5CH_3$). IR 3040 cm$^{-1}$ (m, C—H stretch of alkenes), 2980 cm$^{-1}$, 2950 cm$^{-1}$, 2880 cm$^{-1}$ (s, C-H stretch of alkanes) 1650 cm$^{-1}$ (w, C—C stretch of alkene), 970 cm$^{-1}$ (m, C-H bending of (E)-double bond). CMR (90 MHz, CDCl$_3$) δ 135.4, 132.0, 129.0, 128.6, 127.9, 127.4, 127.1, 125.4, 32.9, 31.8, 29.4, 29.21, 29.17, 26.1, 25.6, 22.6, 20.6, 14.2, 14.0. EIMS (% relative abundance) 260 (0.4), 231 (0.2), 217 (0.1), 191 (0.1), 180 (2.1), 178 (2.8), 161 (1.2), 147 (1.0), 1.33 (1.7), 119 (4.6), 108 (61.1), 93 (25.3), 91 (21.9), 79 (100), 67 (23.8), 55 (16.9).

GC analysis revealed that 92.0% of the product was the desired (Z,Z,Z,E)-3,6,9,11-19:H. The remainder of the product was composed of the (Z,Z,E,E)-isomer (3.0%), the (Z,Z,Z,Z)-isomer (1.0%) and two unknown isomers (4.0%). Purification by HPLC on a Partisil M9 TM 10/50 SCX column, loaded with silver ion and eluted with 0.1% dimethoxyethane in hexane, gave material which was 97.2% pure [0.5% (Z,Z,Z,Z)-isomer, 1.7% (Z,Z,E,E)-isomer and 0.6% unknown isomer]. Analysis: Calc. for $C_{19}H_{32}$: 260.46; C, 87.62; H, 12.38; Found: C, 87.76; H, 12.29.

EXAMPLE 2

Preparation of (Z,Z,Z,Z)-3,6,9,11-nonadecatetraene (B)

To a solution of (Z,Z,Z)-3,6,9-nonadecatrien-11-yne (516 mg, 2 mmol) in 10 ml of dry pentane (0° C.) was added 4.2 ml of 0.5 M dicyclohexylborane in pentane. After 2 h at 0° C., the reaction mixture was diluted with 15 ml of THF and treated with 0.6 ml of glacial acetic acid for 3 h at 50° C. The mixture was then made basic with 4 ml of 5.0 N aqueous sodium hydroxide and treated with 0.86 ml of 30% hydrogen peroxide for 0.5 h. The hexane extract (3×30 ml) was washed with water (3×30 ml), dried over MgSO$_4$ and evaporated to leave an oily residue. Elution of the residue through silica gel (hexane) gave 292 mg (56.2%) of the desired (Z,Z,Z,Z)3,6,9,11-19:H (89% isomeric purity). This material contained (Z,Z,Z,E)3,6,9,11-19:H (1.1%) and 3 major unknown impurities (8.3%). Purification by HPLC on the silver ion-loaded Partisil M9 TM 10/50 SCX column (eluted with 0.1% dimethoxyethane in hexane) yielded material which was greater than 99.0% pure; PMR (360 MHz, C$_6$D$_6$) δ

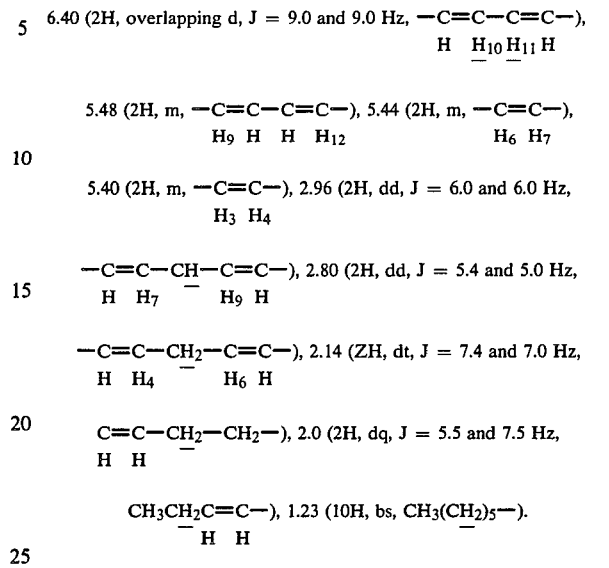

$CH_3CH_2C=C-$), 1.23 (10H, bs, $CH_3(CH_2)_5-$).

0.90 (3H, t, J = 7.5 Hz, $CH_3CH_2C=C-$), 0.88 (3H, t, J=7.0 Hz, $CH_3CH_2CH_2-$). IR 3020 cm$^{-1}$ (m, C—H stretch of alkenes), 2980 cm-hu −1, 2950 cm$^{-1}$, 2880 cm$^{-1}$ (s, C—H stretch of alkanes). CMR (90 MHz, CDCl$_3$) δ132.8, 132.1, 129.4, 128.8, 127.7, 127.1, 123.9, 123.3, 31.8, 29.65, 29.26, 29.17, 27.6, 25.90, 25.60, 22.6, 20.6, 14.21, 14.03. EIMS (% relative abundance) 260 (0.3), 231 (0.2), 217 (0.2), 206 (0.2), 191 (0.1), 180 (1.5), 178 (0.8), 161 (1.2), 147 (1.1), 133 (1.8), 119 (5.0), 108 (67.5), 93 (26.3), 91 (24.1), 79 (100), 67 (25.6), 55 (18.2). Analysis: Calc. for $C_{19}H_{32}$: 260.46. C, 87.62; H, 12.38. Found: C, 87.66, H, 12.32.

EXAMPLE 3

Field Results

Field trapping experiments conducted in 1983 have shown that male fall cankerworm moths are strongly attracted to an insect trap or other locus which contains A or B, individually or in combination. The triene C which captures no male fall cankerworm moths by itself, synergistically enhances the attractiveness of both tetraenes, individually or in combination.

The field tests results summarized in Tables 1 and 2 were performed with commercially available insect traps (Pherocon 1-CP [trademark]), but other traps may be operative. The traps were mounted on posts at a height of 1.5 M and located near host trees. Live female fall cankerworms were held within wire mesh cages near the centre of the trap, while other traps contained synthetic chemical attractants placed within red rubber septa. The results of one test (Table 1) showed that both A and B were good attractants for male fall cankerworm moths at doses of 30 μg and 100 μg. In this experiment, it appeared that A was a more potent attractant than B at a dose of 100 μg. In another experiment, various combinations of the two tetraenes and the triene were compared. The results (Table 2) showed that binary mixtures of either tetraene with the triene were more attractive toward fall cankerworm male moths than either tetraene alone. Effective binary mixtures were comprised of A (50 μg) and C (25 μg), or B (150 μg) and C (25 μg). Neither of the three component mixtures, comprised of the two tetraenes plus the triene, were more effective than the binary mixtures comprised of the triene with either tetraene. A comparison of traps baited with three live virgin female moths to traps baited with a three-component mixture of synthetic attractants A (60 μg), B (15 μg) and C (25 μg) revealed that the synthetic attractant baited traps captured more male moths [mean capture/trap/day = 10.4±11.1 (n=30)] than the live female baited traps [2.99±3.58 (n=133)]. These results indicated that the synthetic attractant was more effective than live females for capturing males.

In accordance with these test results, it is evident that A and B, individually or in combination with C, are effective attractants for male fall cankerworm moths. Using commercial 5×9 mm red rubber septa as carriers, from about 30–500 μg per trap would be effective. However, larger doses may also be effective.

A very wide range of proportions of the triene to either or both tetraenes have been also shown to function as attractants for fall cankerworm moths. In compositions with high proportions of the triene, reduced synergism or simple dilution of the tetraenes may be expected to occur and, dose-response experiments for various compositions comprise the subject of further study. In practice, a less-than-ideal mixture may be tolerated simply by employing a higher dose per trap.

A preliminary trial was conducted to determine the feasibility of mating disruption of the fall cankerworm moth by permeation of the air with synthetic sex attractants. To assess disorientation of male moths to monitoring traps, 8 stakes 1.5 M high were placed in a square 3 M apart to form a test plot 36 M². A rubber septum attached near the top of each stake, was used to release the synthetic attractant A (60 μg), B (15 μg), and C (25 μg). An additional stake (1.5 M high) centered in the test plot, carried a Pherocon 1-CP [trademark] trap baited with a rubber septum containing the three component synthetic attractant used for the disruptant septa. The extent of male orientation disruption was assessed by comparing the number of male moths captured in disruptant plots and in control sites which contained identically baited traps. All disruptant plots and control sites were separated by at least 150 M. The results (Table 3) revealed between 80% to 100% disruption of male orientation to the central monitoring trap and suggests great potential for pheromone-mediated disruption of mating.

TABLE 1

Capture of *A. pometaria* males in traps baited with synthetic (Z,Z,Z,E)-3,6,9,11–19:H or (Z,Z,Z,Z)-3,6,9,11–19:H at various doses

| Lure composition (μg) | Total males captured[a] |
| --- | --- |
| (Z,Z,Z,E)-3,6,9,11–19:H (100) | 73 a |
| (Z,Z,Z,E)-3,6,9,11–19:H (30) | 46 ab |
| (Z,Z,Z,E)-3,6,9,11–19:H (10) | 11 c |
| (Z,Z,Z,E)-3,6,9,11–19:H (3) | 9 c |
| (Z,Z,Z,E)-3,6,9,11–19:H (1) | 3 c |
| (Z,Z,Z,Z)-3,6,9,11–19:H (100) | 35 b |
| (Z,Z,Z,Z)-3,6,9,11–19:H (30) | 28 b |
| (Z,Z,Z,Z)-3,6,9,11–19:H (10) | 2 c |
| (Z,Z,Z,Z)-3,6,9,11–19:H (3) | 3 c |
| (Z,Z,Z,Z)-3,6,9,11–19:H (1) | 1 c |

[a]3× replicated: Pherocon 1-CP [trademark] traps, October 12–14, 1983. Values followed by the same letter are not significantly different (P = 0.05).

TABLE 2

Capture of *A. pometaria* males in Pherocon 1-CP TM traps baited with various combinations of (Z,Z,Z,E)-3,6,9,11–19:H, (Z,Z,Z,Z)-3,6,9,11–19:H, and (Z,Z,Z)-3,6,9–19:H

| Lure composition (μg) | | | |
| --- | --- | --- | --- |
| (Z,Z,Z,E)-3,6,9,11–19:H | (Z,Z,Z,Z)-3,6,9,11–19:H | (Z,Z,Z)-3,6,9–19:H | Total males captured[a] |
| 120 | 30 | 50 | 109 a |
| 50 | 150 | 25 | 97 ab |
| 0 | 150 | 25 | 92 ab |
| 50 | 0 | 25 | 80 ab |
| 50 | 150 | 0 | 55 bc |
| 50 | 0 | 0 | 35 c |
| 0 | 150 | 0 | 38 c |

[a]6× replicated: Pherocon 1-CP TM traps, October 19–22, 1983. Values followed by the same letter are not significantly different (P = 0.05)

TABLE 3

Capture of *A. pometaria* males Pherocon 1-CP TM traps in untreated plots and plots treated with (Z,Z,Z,E)-3,6,9,11–19:H + (Z,Z,Z,Z)-3,6,9,11–19:H + (Z,Z,Z)-3,6,9–19:H

| | Total males captured[a] | | |
| --- | --- | --- | --- |
| Date | Disruptant plots | Control plots | % Disruption[b] |
| Oct. 4 | 2 | 10 | 80 |
| Oct. 5 | 2 | 19 | 89 |
| Oct. 6 | 0 | 4 | 100 |
| Oct. 7 | 9 | 65 | 86 |

[a]Total number of males caught in 3× replicated treatments.

$$^b\% \text{ Disruption} = \frac{\left(\begin{array}{c}\text{Number caught in}\\ \text{control plots}\end{array}\right) - \left(\begin{array}{c}\text{Number caught in}\\ \text{disruptant plots}\end{array}\right)}{\text{Number captured in control plots}} \times 100$$

We claim:

1. Essentially pure polyunsaturated straight chain hydrocarbons of nineteen carbon atoms having double bonds in the 3, 6 and 9 positions in the Z-configuaration, and the bond in the 11-position being selected from a double bond in the Z-configuration and a double bond in the E-configuration.

2. The compound of claim 1 which is (Z,Z,Z,E)-3,6,9,11-nonadecatetraene (A).

3. The compound of claim 1 which is (Z,Z,Z,Z)-3,6,9,11-nonadecatetraene (B).

4. An insect attractant dose comprising an essentially pure form of at least 30 μg of at least one of (Z,Z,Z,E)-3,6,9,11-nonadecatetraene and (Z,Z,Z,Z)-3,6,9,11-nonadecatetraene in combination with a selected insect attractant carrier.

5. An insect attractant comprising a synergistically active proportion of (Z,Z,Z)-3,6,9,-nonadecatriene and the composition of claim 4.

6. The mixture of claim 5 wherein the proportion of (Z,Z,Z)-3,6,9-nonadecatriene is less than about 90% w/w based on the weight of synergistically interactive components.

7. The mixture of claim 6 wherein the proportion of (Z,Z,Z)-5,6,9-nonadecatriene is about 33% w/w based on the weight of synergistically interactive components.

8. The composition of claim 4 wherein said carrier is one of a solid and a liquid carrier.

9. The composition of claim 4 wherein said carrier is a rubber carrier.

10. The composition of claim 4 placed in an insect trap.

11. A method of attracting fall cankerworm moths, during the flight season and in the expected locale of such moths, to at least one specific locus, comprising baiting an insect trap with the composition of claim 4.

12. A method of confusing fall cankerworm moths, during the flight season and in the expected locale of such moths, comprising at least one of disseminating and baiting specific loci with the composition of claim 4.

* * * * *